United States Patent
Jauvtis et al.

(10) Patent No.: US 11,116,595 B2
(45) Date of Patent: Sep. 14, 2021

(54) GUIDING AND SUPPORT DEVICE, PARTICULARLY FOR A ROBOT FOR MINIMALLY-INVASIVE SURGERY THROUGH A SINGLE PARIETAL INCISION AND/OR NATURAL ORIFICE

(71) Applicant: VALUEBIOTECH S.R.L., Milan (IT)

(72) Inventors: Louis Judah Jauvtis, Evilard (CH); Nicolò Donella, Milan (IT); Renzo Zaltieri, Trezzano Rosa (IT); Federica Iovine, Falciano di Caserta (IT); Filippo Righetto, Milan (IT); Alberto Giovanni Pansini, Catania (IT); Antonello Forgione, Milan (IT)

(73) Assignee: VALUEBIOTECH S.R.L., Milan (IT)

( * ) Notice: Subject to any disclaimer, the term of this patent is extended or adjusted under 35 U.S.C. 154(b) by 624 days.

(21) Appl. No.: 16/076,171

(22) PCT Filed: Feb. 11, 2016

(86) PCT No.: PCT/IB2016/050726
§ 371 (c)(1),
(2) Date: Aug. 7, 2018

(87) PCT Pub. No.: WO2017/137806
PCT Pub. Date: Aug. 17, 2017

(65) Prior Publication Data
US 2021/0186635 A1    Jun. 24, 2021

(51) Int. Cl.
*A61B 34/30* (2016.01)
*A61B 34/00* (2016.01)
(Continued)

(52) U.S. Cl.
CPC .............. *A61B 34/71* (2016.02); *A61B 34/30* (2016.02); *A61B 90/50* (2016.02); *B25J 5/007* (2013.01); *B25J 5/02* (2013.01)

(58) Field of Classification Search
CPC ..... A61B 34/30; A61B 34/71; A61B 17/3403; A61B 90/50; A61B 19/201; A61B 19/203;
(Continued)

(56) References Cited

U.S. PATENT DOCUMENTS

| 2014/0251043 A1 | 9/2014 | Gale et al. |
| 2017/0225340 A1* | 8/2017 | Donella ................... B25J 17/02 |

FOREIGN PATENT DOCUMENTS

| DE | 202012000521 U1 | 4/2012 |
| WO | 2012059791 A1 | 5/2012 |

(Continued)

OTHER PUBLICATIONS

International Search Report dated Oct. 28, 2016 re: Application No. PCT/IB2016/050726, pp. 1-4, WO 2014/173932 A1, WO 2012/059791 A1, US 2014/251043 A1, WO 2014/129362 A1 and DE 20 2012 000521 U1.

(Continued)

*Primary Examiner* — Vi X Nguyen
(74) *Attorney, Agent, or Firm* — Cantor Colburn LLP

(57) ABSTRACT

A guiding and support device, particularly for a robot for minimally-invasive surgery through a single parietal incision and/or natural orifice, includes mutually associated rigid bodies, and stiffening elements associated with the guiding and support device and adapted for the transition of the device from an inactive configuration, the rigid bodies can move with respect to each other, to an active configuration, in which the rigid bodies are mutually aligned so as to define a rigid guide, and vice versa. The device further includes
elements for combined rotary and translational motion which are adapted, in the active configuration of the guiding and support device, to translate and/or to rotate a robot.

11 Claims, 11 Drawing Sheets

(51) Int. Cl.
*B25J 5/02* (2006.01)
*A61B 90/50* (2016.01)
*B25J 5/00* (2006.01)

(58) Field of Classification Search
CPC ..... A61B 19/20; A61B 19/22; A61B 19/2203; A61B 19/5244
See application file for complete search history.

(56) References Cited

FOREIGN PATENT DOCUMENTS

| | | |
|---|---|---|
| WO | 2014129362 A1 | 8/2014 |
| WO | 2014173932 A1 | 10/2014 |

OTHER PUBLICATIONS

Written Opinion dated Oct. 28, 2016 re: Application No. PCT/IB2016/050726, pp. 1-5, WO 2014/173932 A1.

* cited by examiner

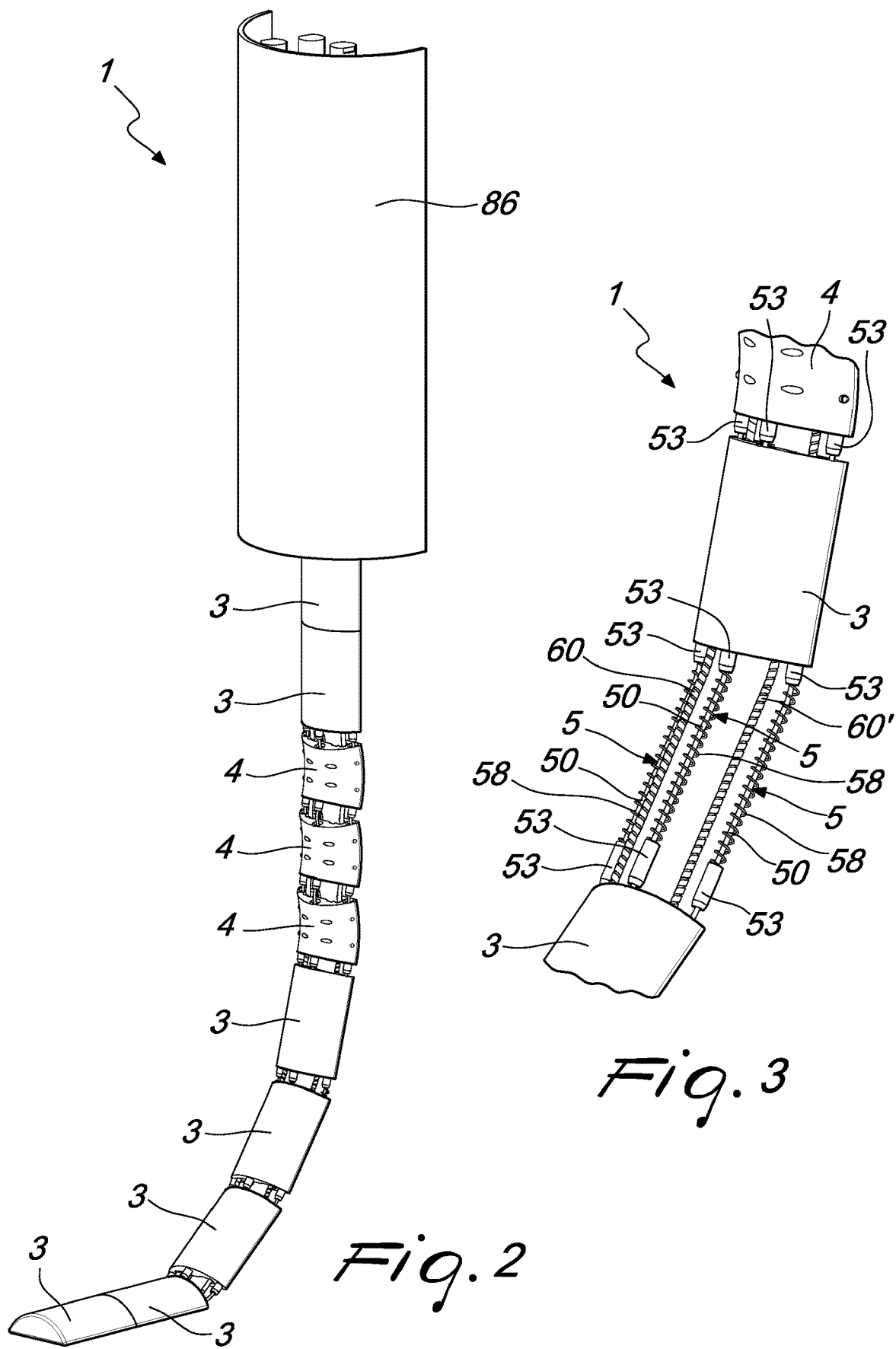

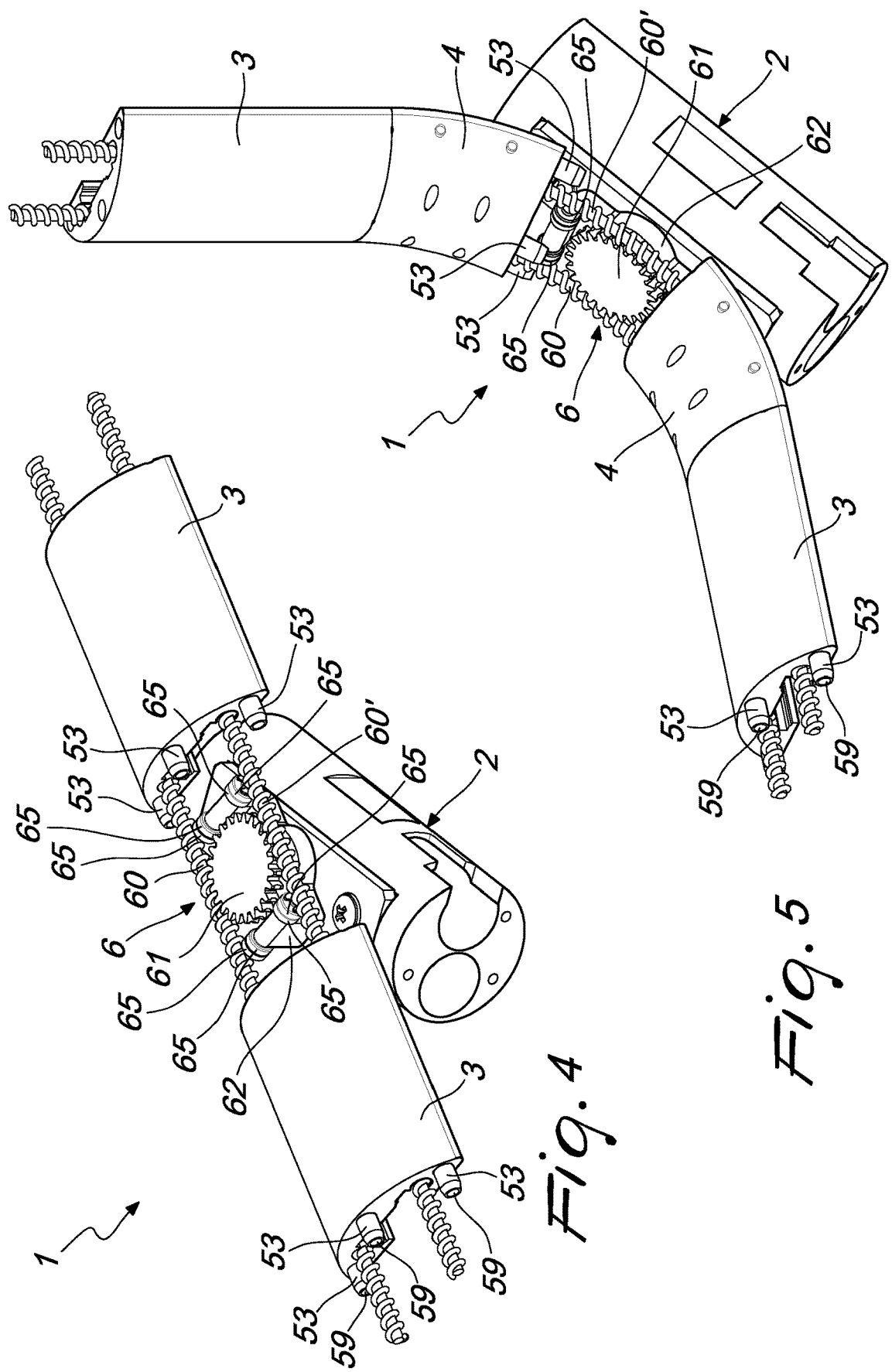

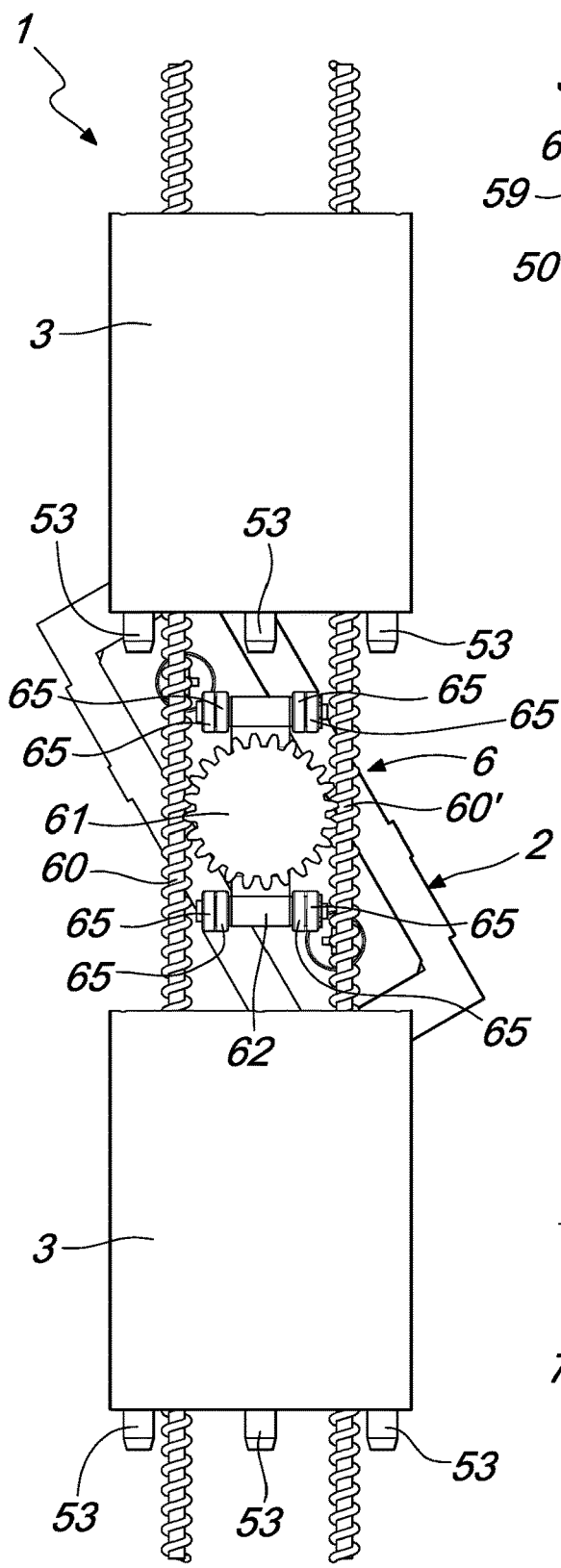
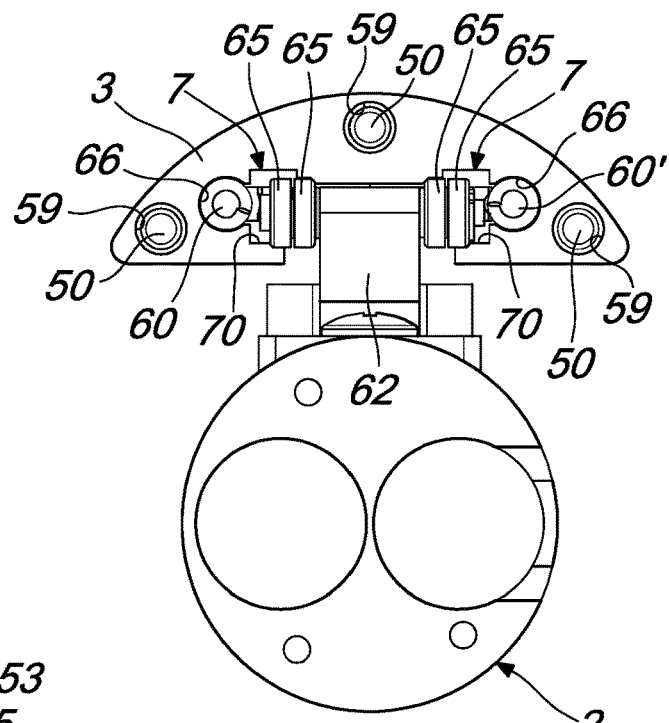
Fig. 8
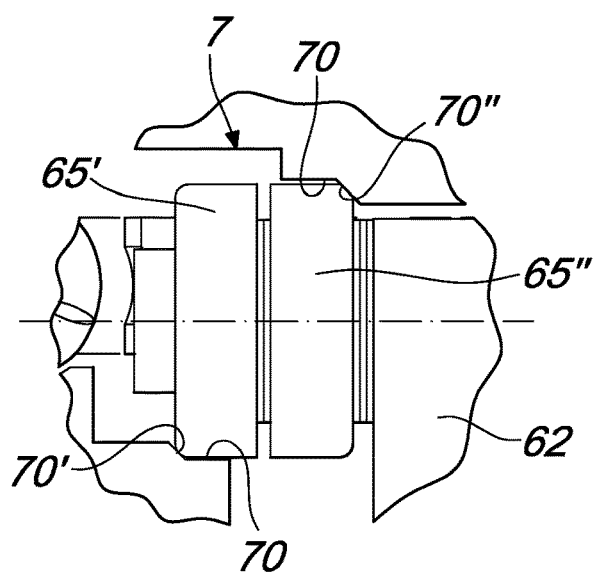
Fig. 9
Fig. 7

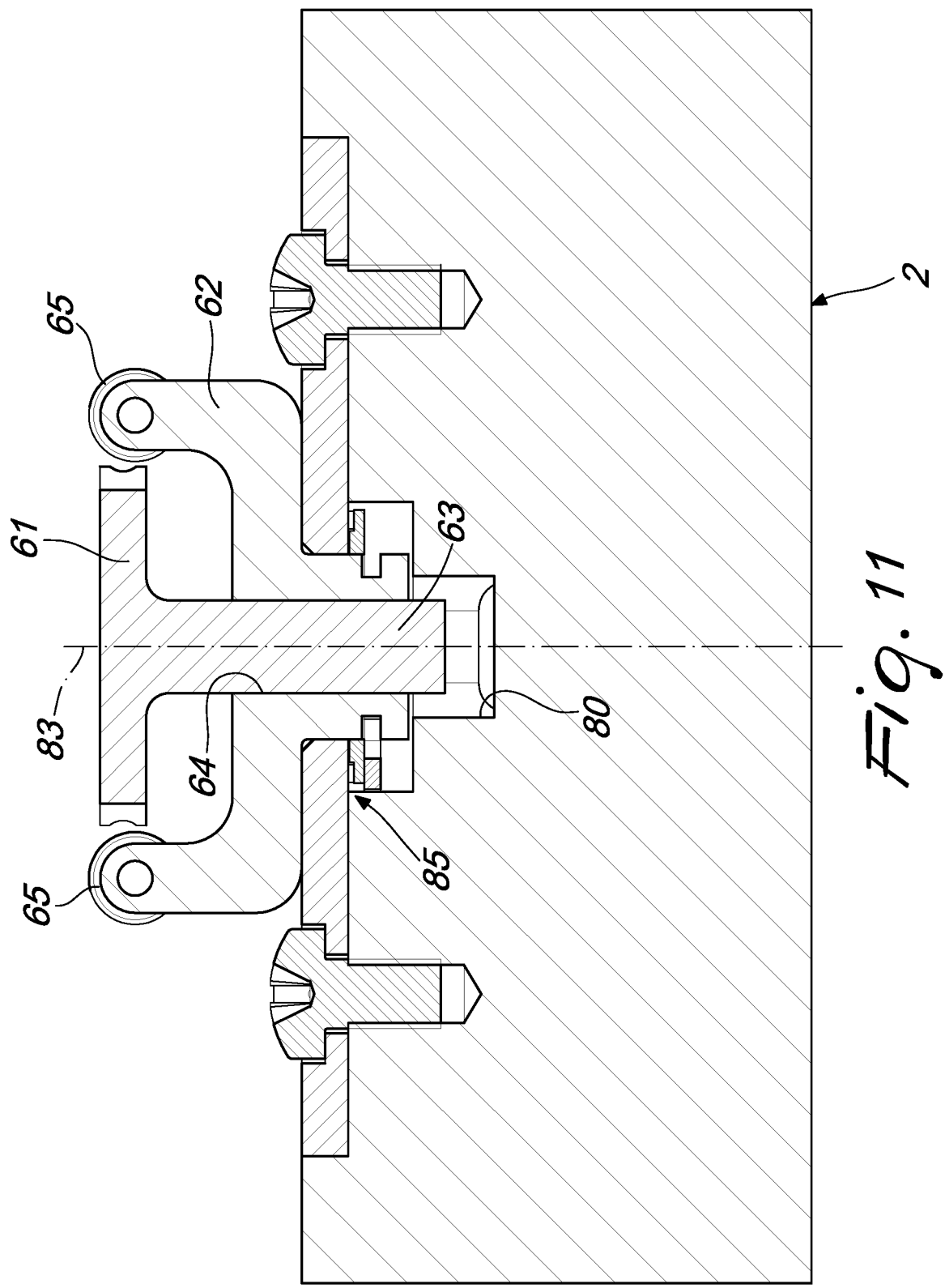

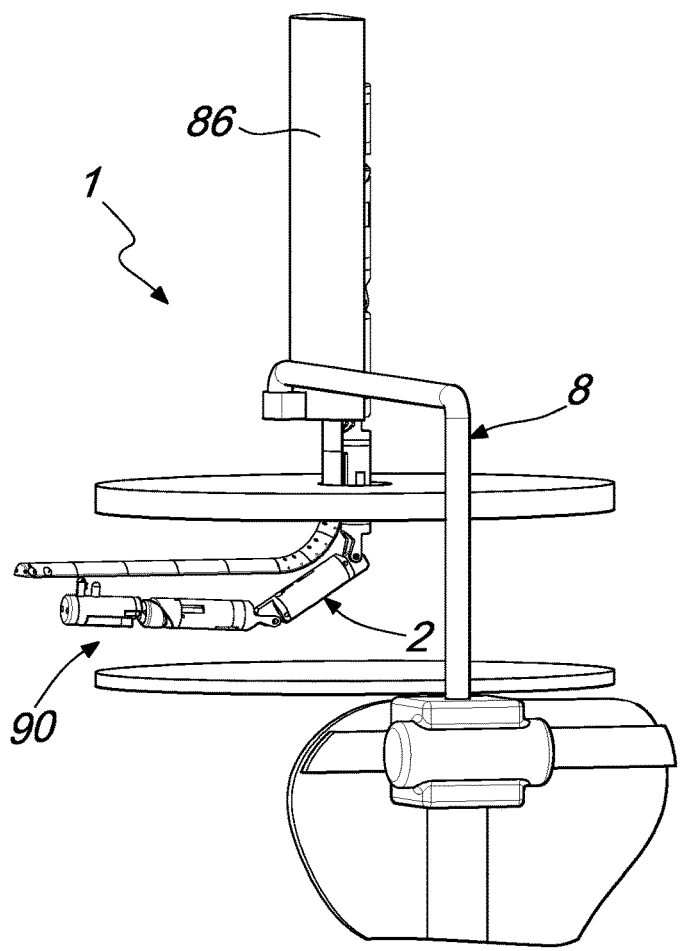
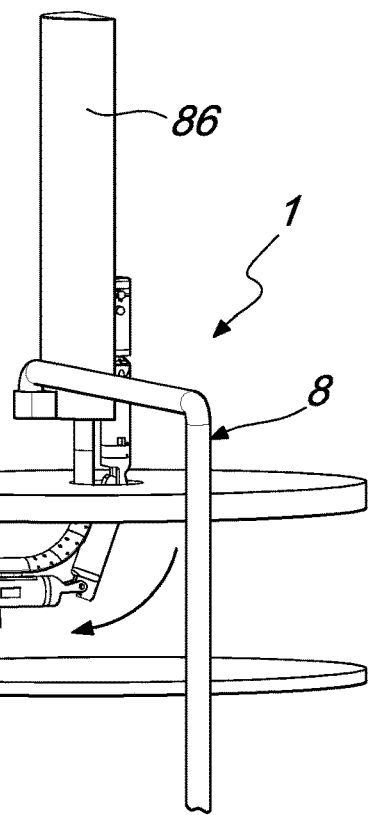
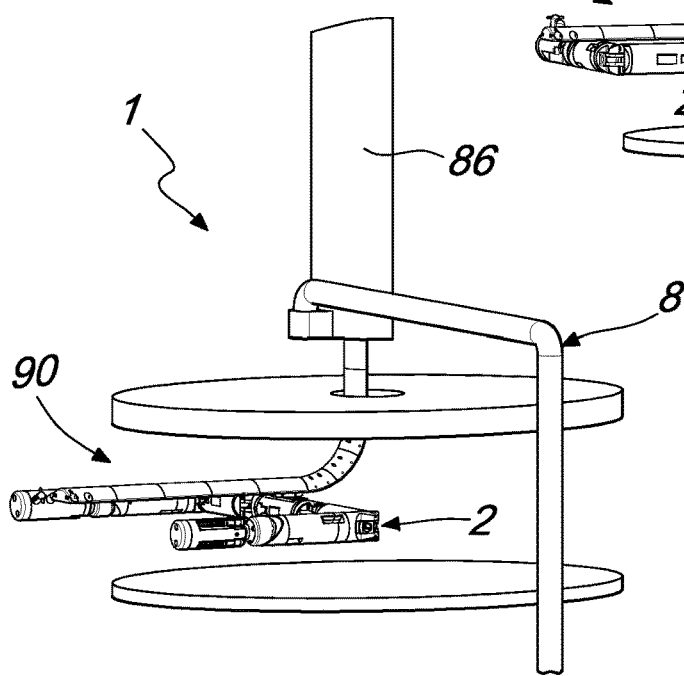
Fig. 14
Fig. 15
Fig. 16

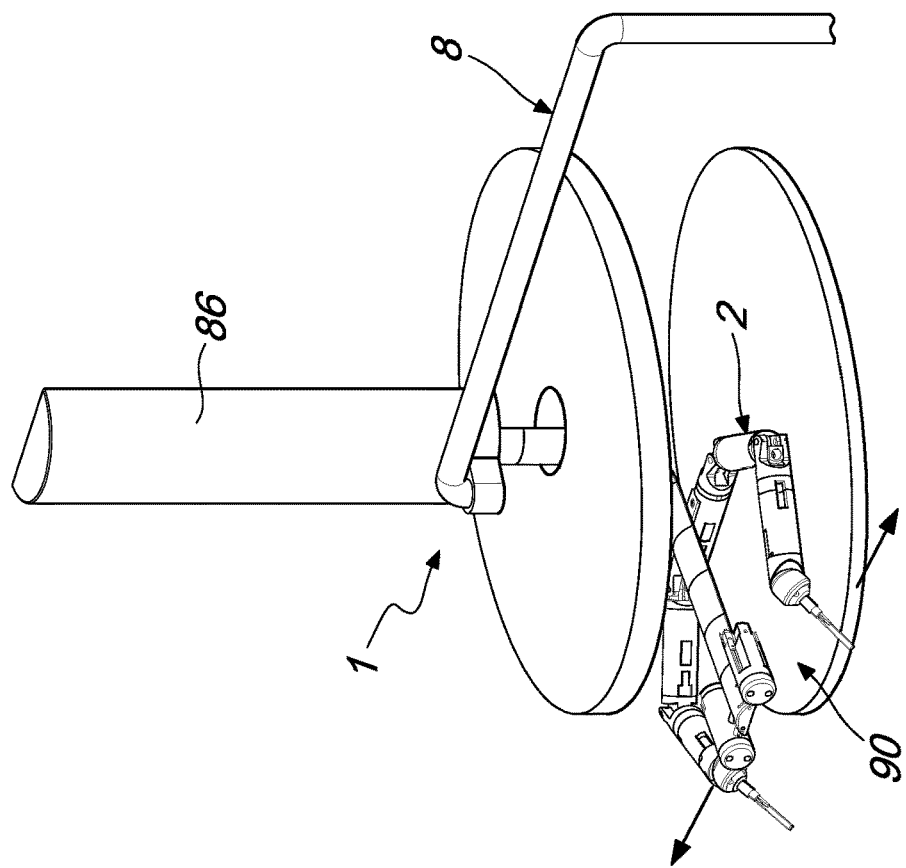
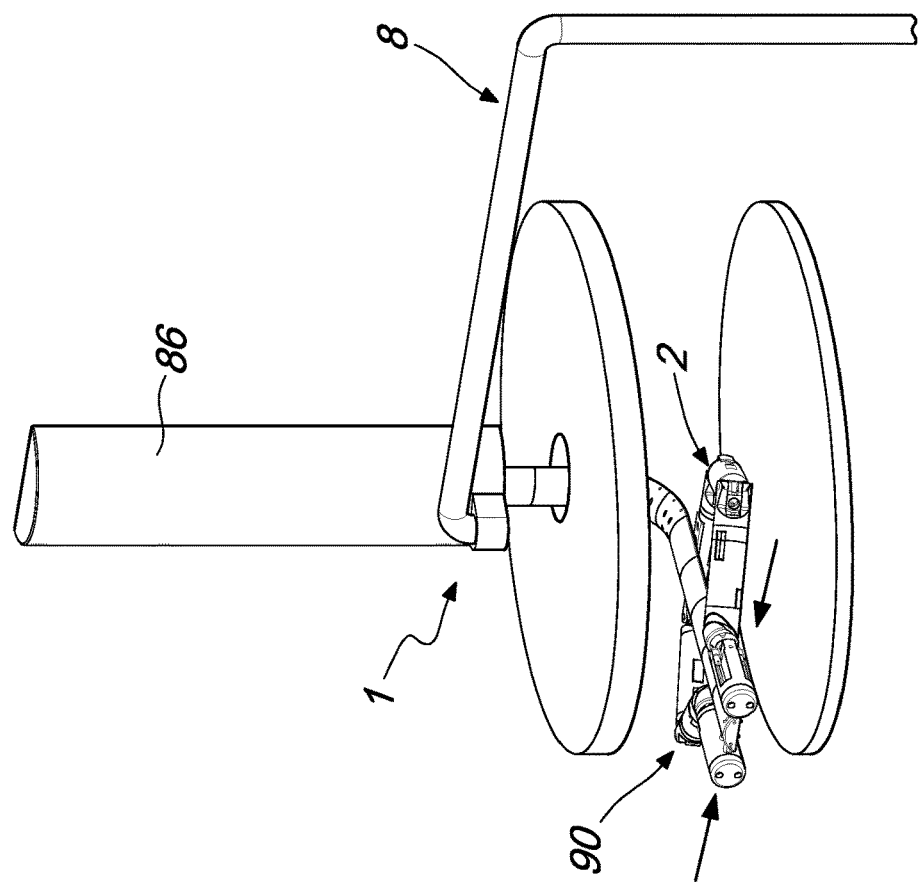

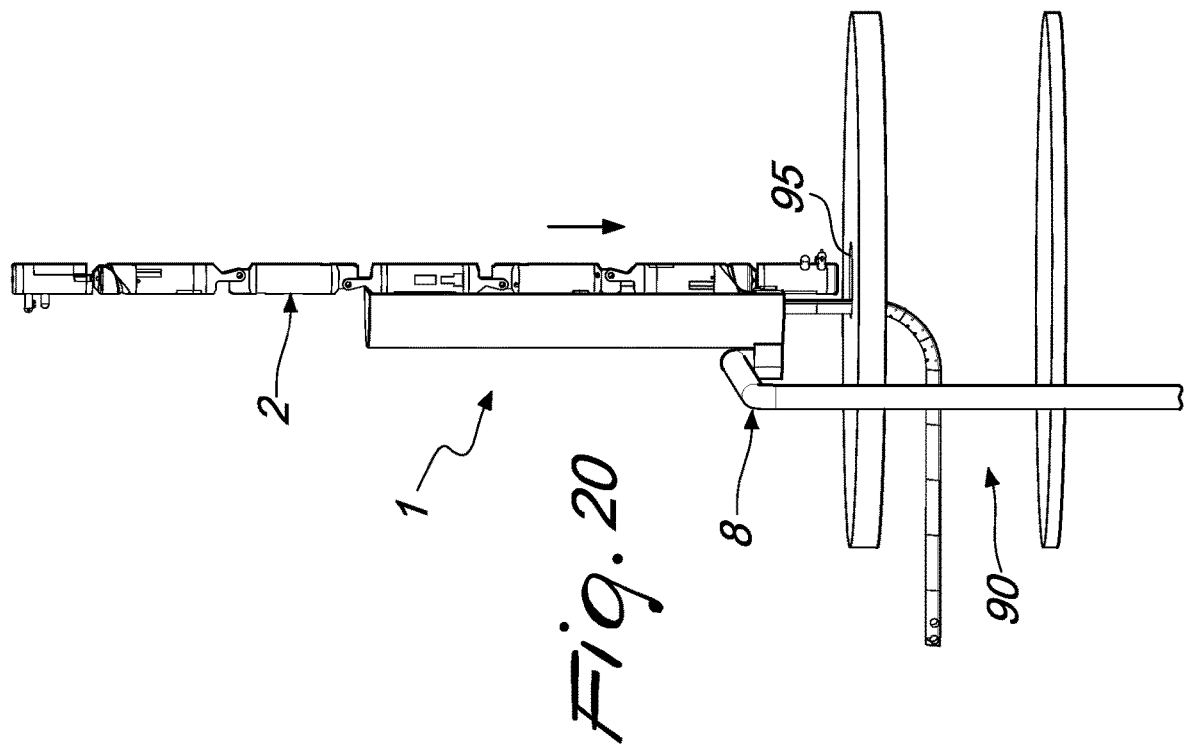
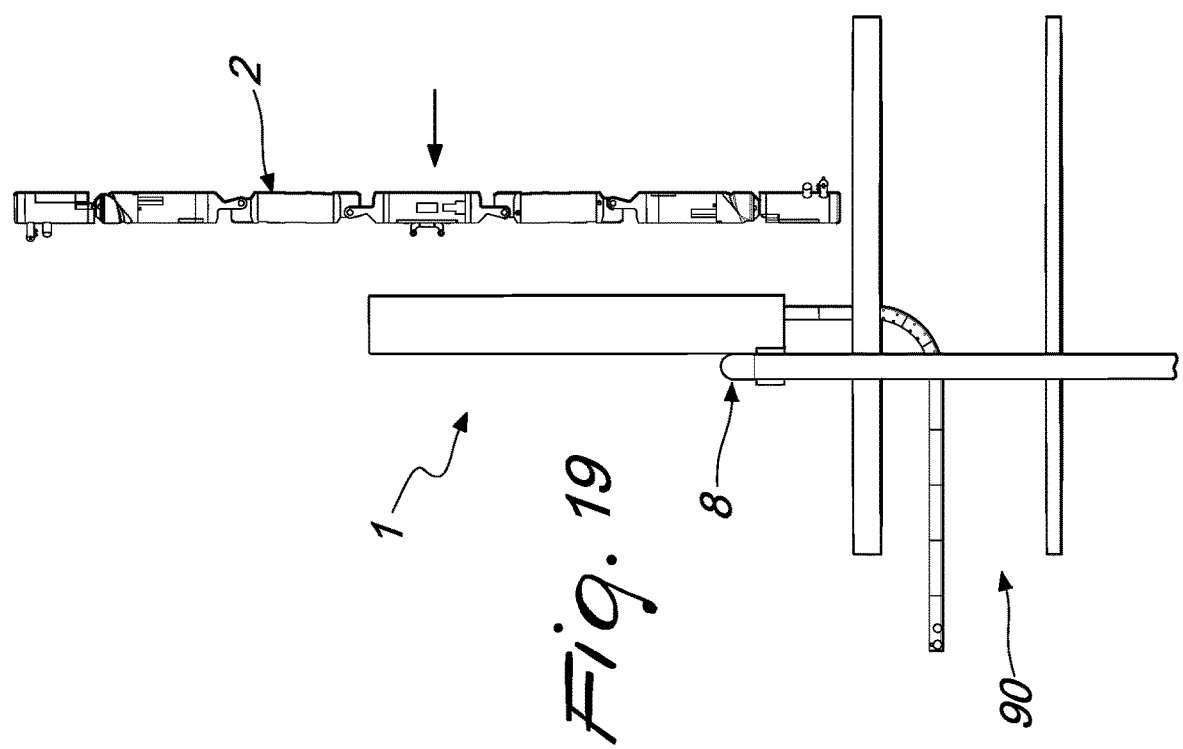

GUIDING AND SUPPORT DEVICE, PARTICULARLY FOR A ROBOT FOR MINIMALLY-INVASIVE SURGERY THROUGH A SINGLE PARIETAL INCISION AND/OR NATURAL ORIFICE

TECHNICAL FIELD

The present disclosure relates to a guiding and support device, particularly for a robot for minimally-invasive surgery through a single parietal incision and/or natural orifice.

BACKGROUND

The use of minimally-invasive techniques has now become the standard for many routine surgical procedures, and as a consequence the sector of robotic surgery is also seeing the continual development of, and experimentation with, new miniaturized robotic devices, such as, for example, the robotic device disclosed in international patent application no. WO2014173932A1 by the same applicant.

An inherent difficulty in the surgical operations that can be carried out by way of such miniaturized robotic devices involves the correct introduction and positioning of the robotic device in the surgical area of interest, through parietal incisions and/or natural orifices present in the patient.

The introduction of a miniaturized robotic device into the patient inside a surgical area is in fact a very critical operation, in that it needs to be as non-invasive as possible.

Likewise, the correct positioning and orientation of the robotic device with respect to a reference system integral with the patient, once the surgical area of interest has been reached, is also very critical, in that the correct execution of the surgical operation depends on it.

SUMMARY

The aim of the present disclosure provides a guiding and support device, particularly for a robot for minimally-invasive surgery through a single parietal incision and/or natural orifice, which solves the above mentioned technical problems, by making it possible to introduce and correctly position a miniaturized robotic device inside a surgical area of interest.

Within this aim, the present disclosure provides a guiding and support device that is particularly adapted to introduce and position a robotic device such as that disclosed in international patent application no. WO2014173932A1 by the same applicant.

The disclosure provides a guiding and support device that makes it possible to introduce, and extract, a miniaturized robotic device inside a surgical area through a single parietal incision and/or by way of a natural orifice.

The disclosure also provides a guiding and support device that makes it possible to stably and safely support a robotic device during all the steps of the surgical operation.

The disclosure further provides a guiding and support device that can define a curvilinear guide for the introduction of a robot for minimally-invasive surgery in a surgical area.

The disclosure further provides a guiding and support device the length of which can be varied according to requirements and to the location of the surgical area to be reached.

The disclosure provides a guiding and support device that is capable of offering the widest guarantees of reliability and safety in use.

This aim and these and other advantages which will become better apparent hereinafter are achieved by providing a guiding and support device, particularly for a robot for minimally-invasive surgery through a single parietal incision and/or natural orifice, which comprises:

a plurality of mutually associated rigid bodies, stiffening means associated with said guiding and support device and adapted for the transition of said device from an inactive configuration, in which said rigid bodies can move with respect to each other, to an active configuration, in which said rigid bodies are mutually aligned so as to define a rigid guide, and vice versa, means for combined rotary and translational motion which are adapted, in said active configuration of said guiding and support device, to translate and/or rotate a robot along said guide, characterized in that said means for combined rotary and translational motion comprise a pair of flexible threaded shafts, and a gearwheel configured to engage said pair of flexible threaded shafts, wherein the rotation of said flexible threaded shafts determines the translation of said gearwheel along said guide and/or the rotation of said gearwheel with respect to its own axis, said gearwheel being adapted to be associated rigidly with a robot.

BRIEF DESCRIPTION OF THE DRAWINGS

Further characteristics and advantages of the disclosure will become better apparent from the description of a preferred, but not exclusive, embodiment of a guiding and support device, particularly for a robot for minimally-invasive surgery through a single parietal incision and/or natural orifice, which is illustrated by way of non-limiting example with the aid of the accompanying drawings wherein:

FIG. 2 is a perspective view of only the guiding and support device in FIG. 1, according to the disclosure;

FIG. 3 is an enlarged view of the guiding and support device in FIG. 2, according to the disclosure, in which one of the rigid bodies that make up the device has been removed;

FIG. 4 is a perspective view of a portion of the guiding and support device, according to the disclosure, associated with a component of a robot for minimally-invasive surgery, and in which one of the rigid bodies that make up the device has been removed;

FIG. 5 is a perspective view of a different portion of the guiding and support device, according to the disclosure;

FIG. 7 is a plan view from above of the portion of the guiding and support device shown in FIG. 4;

FIG. 8 is a front elevation view of a portion of the guiding and support device, according to the disclosure, associated with a component of a robot for minimally-invasive surgery;

FIG. 9 is an enlarged portion of FIG. 8;

FIG. 11 is a transverse cross-sectional view of a carriage belonging to the guiding and support device, according to the disclosure, associated with a component of a robot for minimally-invasive surgery;

FIGS. 12 to 18 show a succession of steps of the procedure for introducing and positioning a robot for minimally-invasive surgery inside a surgical area, by way of the guiding and support device according to the disclosure; and FIGS. 19 and 20 show two initial, successive steps of a different procedure for inserting a robot for minimally-invasive surgery inside a surgical area, by way of the guiding and support device according to the disclosure.

DETAILED DESCRIPTION OF THE DRAWINGS

Figure 1:
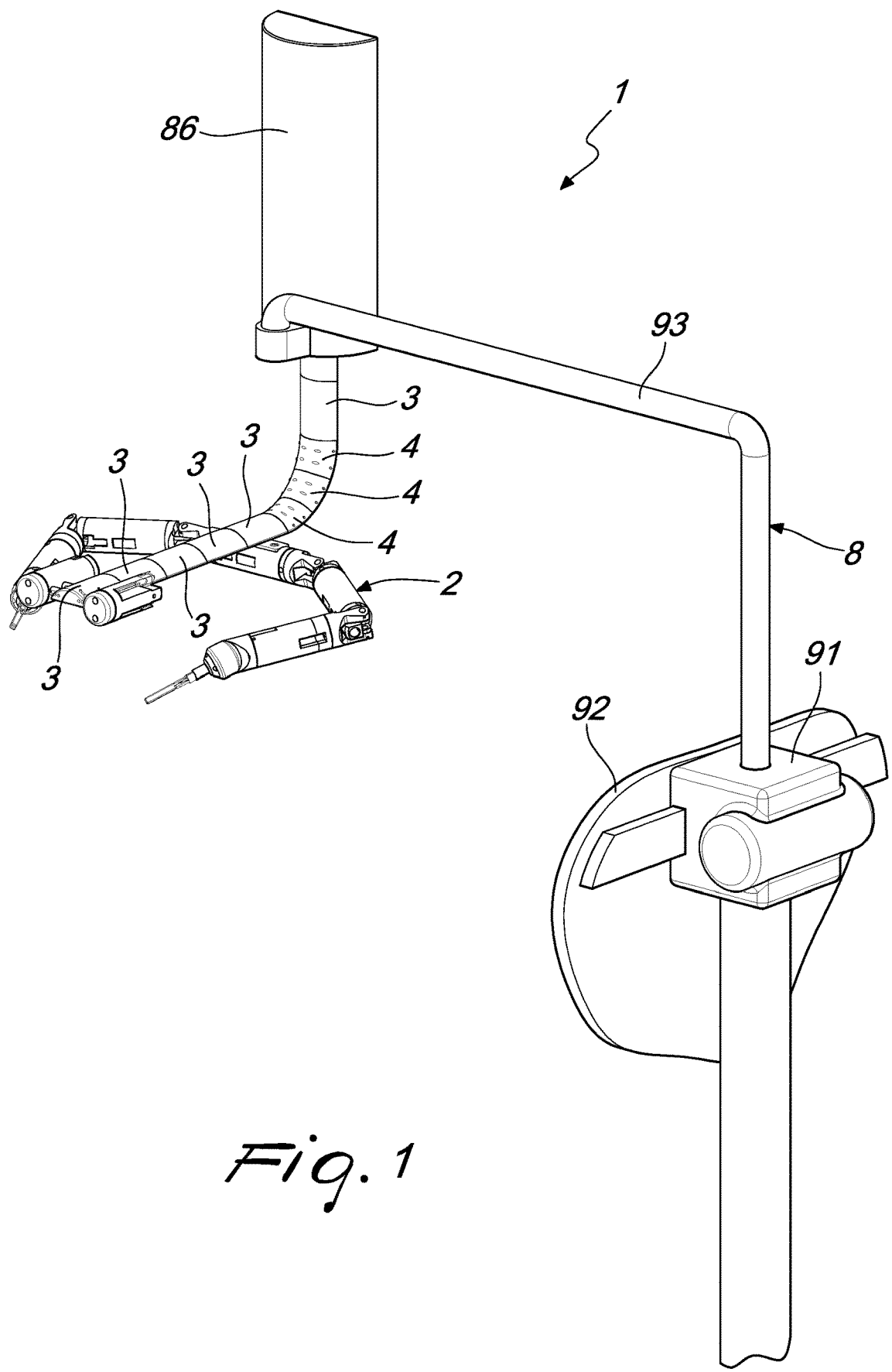
FIG. 1 is a perspective view of an embodiment of a guiding and support device, according to the disclosure, supporting a robot for minimally-invasive surgery in an active configuration.

With reference to FIGS. 1-20, the guiding and support device, generally designated by the reference numeral 1, is particularly adapted to guide and support a robot 2 for minimally-invasive surgery through a single parietal incision and/or natural orifice, and it comprises:

a plurality of mutually associated rigid bodies 3, 4, stiffening means 5 associated with the guiding and support device 1 and adapted for the transition of the device 1 from an inactive configuration, in which the rigid bodies 3, 4 can move with respect to each other, to an active configuration, in which the rigid bodies 3, 4 are mutually aligned so as to define a rigid guide 7, and vice versa;

means 6 for combined rotary and translational motion which are adapted, in the active configuration of the device 1, to translate and/or rotate a robot 2 along such guide 7.

According to the disclosure, the means for combined rotary and translational motion 6 comprise a pair of flexible threaded shafts 60, 60', and a gearwheel 61 configured to engage such pair of flexible threaded shafts 60, 60', wherein the rotation of the flexible threaded shafts 60, 60' determines the translation of the gearwheel 61 along the guide 7 and/or the rotation of the gearwheel 61 with respect to its own axis. The gearwheel 61 is adapted to be associated rigidly with a robot 2.

The flexible threaded shafts 60, 60', since they are flexible, are configured to be deformed, curving, as a function of the curvilinear shape assumed by the guiding and support device 1 in the active configuration thereof.

The rigid bodies 3, 4 comprise preferably at least a first group of straight rigid bodies 3 and a second group of curved rigid bodies 4. In this manner, in its active configuration, the guiding and support device 1 assumes a curvilinear configuration, i.e. a configuration that has at least one curved portion.

Furthermore, the straight rigid bodies 3 and the curved rigid bodies 4 can be mutually associated so that the rigid guide 7 assumes a variable curvilinear configuration and has a variable length.

In other words, the length of the guide 7 is variable on the basis of the number of rigid bodies 3, 4 that it is envisaged to mutually associate.

Furthermore, the curvilinear shape assumed by the guide 7 is also variable by differently mutually drawing together straight rigid bodies 3 and curved rigid bodies 4.

Preferably, the means for combined rotary and translational motion 6 comprise a carriage 62 which can slide along the guide 7 and is coupled so that it can translate to the gearwheel 61 and is adapted to be coupled so that it can translate to the robot 2.

Preferably, the gearwheel 61 comprises a shaft 63 which passes through a hole 64 provided in the carriage 62. The robot 2 is therefore adapted to be coupled so that it can rotate to such shaft 63 of the gearwheel 61, so as to be able to rotate about the axis 83.

The shaft 63 is adapted to engage with a corresponding recess 80 present in the robot 2 by way of shape mating. The shaft 63 can in fact comprise, at its end intended to engage with the recess 80, an at least partially squared portion 81, adapted to be associated with a corresponding at least partially squared portion 82 of the recess 80, so that the rotation of the gearwheel 61 is transmitted to the robot 2 and causes the rotation thereof about the axis 83.

Such rotation however is not transmitted to the carriage 62, in that the shaft 63, which passes through the hole 64 present in the carriage 62, is free to rotate about the axis 83, inside the hole 64.

Advantageously, in fact, the carriage 62 is connected to the robot 2 by way of a rotating joint 85.

The shaft 63 is adapted to slide freely with respect to the carriage 62 and to the robot 2 along the axis 83, i.e. in a direction perpendicular to the direction of motion of the carriage 62 along the guide 7. In this manner it is ensured that the robot 2 can transit the curvilinear portions of the guide 7 as well. In fact, the wheels 65 of the carriage 62 remain coupled to the track 70, while the gearwheel 61 remains meshed to the two flexible threaded shafts 60, 60' and in the transit through a curved portion the relative distance between the gearwheel 61 and the carriage 62, along the axis 83, varies.

In each one of the rigid bodies 3, 4 there is advantageously at least one track 70, which defines the guide 7. The carriage 62 can comprise a plurality of wheels 65 which are configured to move along the track 70.

Preferably each one of the rigid bodies 3, 4 comprises a pair of longitudinal cavities 66 which accommodate the flexible threaded shafts 60, 60' so that they can rotate about their own longitudinal axes inside the longitudinal cavities 66.

The guiding and support device 1 advantageously comprises a pair of motor means 67, which are adapted to turn, independently of each other, the flexible threaded shafts 60, 60' about their own longitudinal axes.

In the embodiment of the guiding and support device 1 shown in the accompanying figures, the motor means 67 are advantageously accommodated in a box-like body 86 which is preferably arranged outside the surgical area 90.

The rotation of the two flexible threaded shafts 60, 60' at the same speed, and in the same direction, is advantageously adapted to make the gearwheel 61 and therefore the robot 2 translate along the guide 7, while the rotation of the two flexible threaded shafts 60, 60' at the same speed, but in opposite directions, is adapted to make the gearwheel 61 and therefore the robot 2 rotate about the axis 83.

A difference in rotation speed between the flexible threaded shafts 60, 60' produces a combined rotary and translational motion of the gearwheel 61 and therefore of the robot 2.

Preferably, the motor means 67 transmit the rotation to the flexible threaded shafts 60, 60' by way of rigid shafts 68 which are adapted to absorb the axial loads originating from the flexible threaded shafts 60, 60'.

The stiffening means 5 comprise preferably at least one tensioning cable 50 which passes through each of the rigid bodies 3, 4 and can be actuated by motor means 51 which are adapted to place the cable 50 under tension. Preferably there is a plurality of tensioning cables 50.

The active configuration of the device 1 is advantageously obtained by shape mating of a female element 52 with a male element 53 of two consecutive rigid bodies 3, 4. When the tensioning cables 50 are placed under tension by the corresponding motor means 51, the female 52 and male 53 elements mate with each other and render the device 1 rigid.

For example, the male elements 53 can be constituted by conical elements, designed to be inserted into corresponding female elements 52 shaped like a conical recess, so as to ensure that, in the active configuration of the guiding and support device 1, the rigid bodies 3, 4 are correctly aligned with respect to each other.

Figure 6:
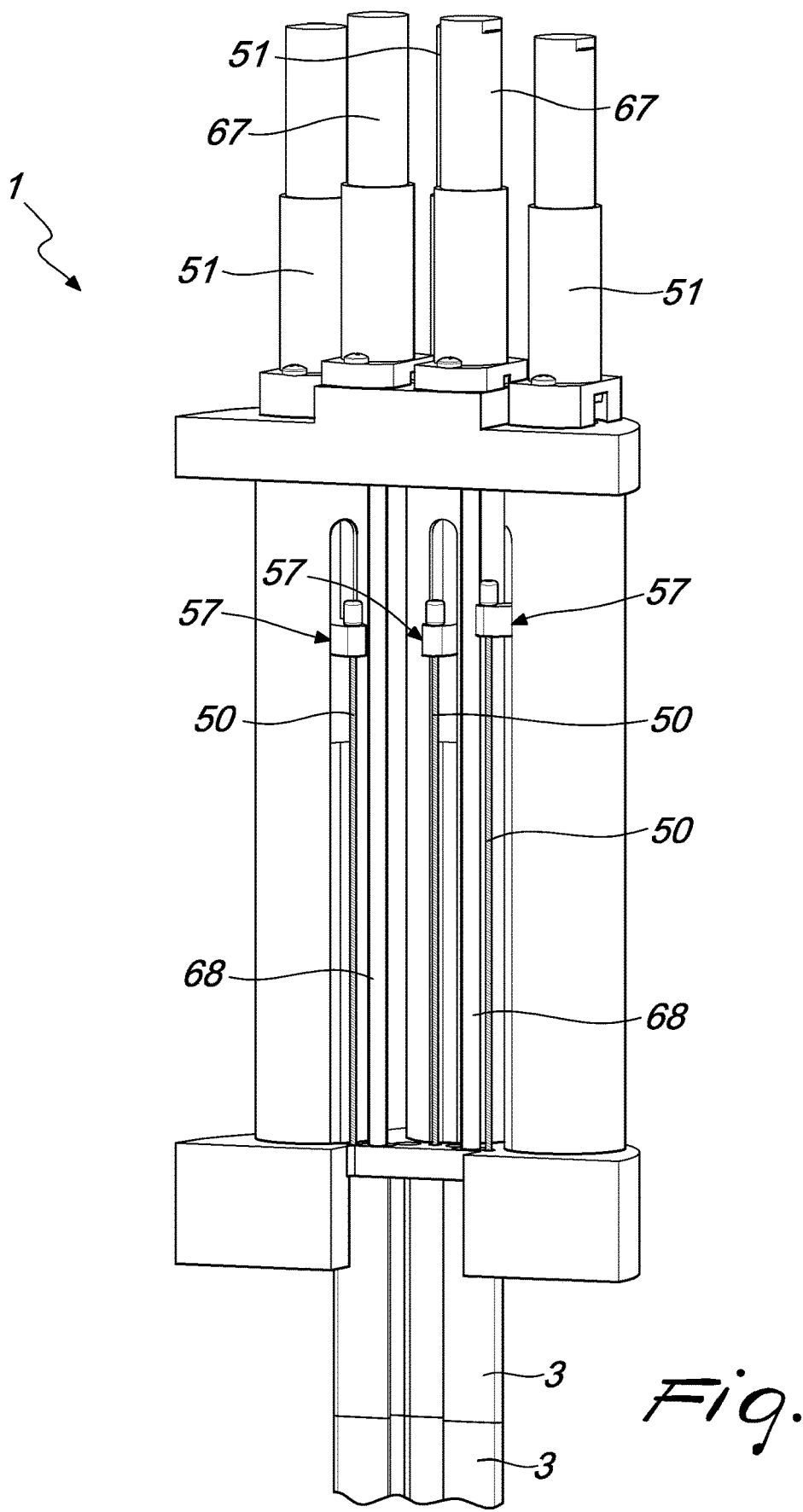
FIG. 6 is a perspective view of the means of actuating the guiding and support device, according to the disclosure.

As illustrated by way of example in FIG. 6, there can be a motor means 51 for each tensioning cable 50, where each motor means 51 can be actuated independently of the others.

The tensioning cables 50 can be placed under tension by way of a leadscrew mechanism 57. The leadscrew mechanism 57 comprises a female thread connected to an end of the tensioning cable 50, and a screw actuated by the motor means 51. The other end of the tensioning cable 50 is fixed to the end rigid body 3 of the guiding and support device 1.

Alternatively, the tensioning cables 50 can also be placed under tension by way of linear actuators or pulley systems.

Alternatively there can be a single motor means which is configured to place all the tensioning cables 50 under tension. In this case, the tensioning cables 50 can be connected, by way of springs, to a single connecting cable which is actuated by the motor means, so as to compensate any differences in the length of the cables and balance the forces generated by the traction of the connecting cable on the tensioning cables.

The rigid bodies 3, 4 can comprise through holes 59 which slideably accommodate the tensioning cables 50.

As illustrated in FIG. 3, between two male elements 53 of two contiguous rigid bodies 3, 4 there can be a spring 58, coaxial to the tensioning cable 50 and also accommodated in the through hole 59, which is adapted to exert a separation force between the male elements 53 of two contiguous rigid bodies 3, 4. In fact, between the male elements 53 and the female elements 52 there can be a mating with interference which necessitates an elastic separation force for the device 1 to be able to pass from the rigid active configuration, in which the rigid bodies 3, 4 are associated with each other, to the inactive configuration, in which the rigid bodies 3, 4 are separate from each other and movable with respect to each other.

Figure 10:
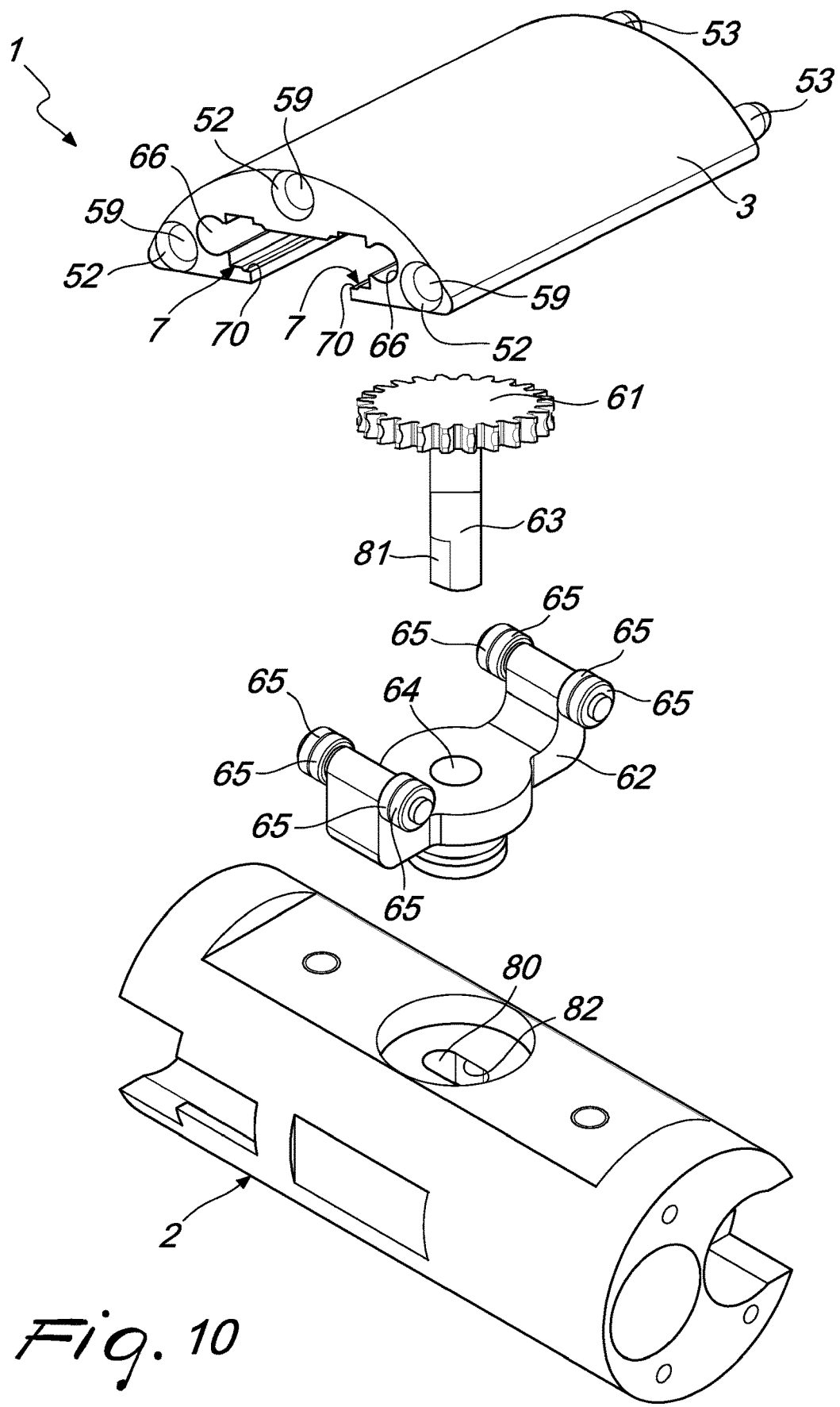
FIG. 10 is an exploded perspective view of some components of the guiding and support device, according to the disclosure, and also of a component of a robot for minimally-invasive surgery.

Advantageously, as illustrated in FIG. 10, the through holes 59 can pass through, and be coaxial to, the female elements 52 and the male elements 53.

The carriage 62 comprises preferably four groups of pairs of wheels 65, wherein each pair of wheels comprises a first wheel 65' which has a first point of contact 70' with a first portion of the track 70 and a second wheel 65" which has a second point of contact 70" with a second portion of the track 70.

Each wheel 65, 65', 65" can rotate independently of every other wheel.

The wheels 65' and 65" of each pair of wheels 65 therefore have respectively two points of contact 70' and 70" with the track 70, which are separate and mutually opposite.

The carriage 62 is therefore adapted to be connected to the track 70 in a stable manner and without significant mechanical play, so that the corresponding movement between the carriage 62 and the track 70 proper is limited to only the translation along the track 70 proper.

The carriage 62 is advantageously adapted to absorb the loads that are developed in the combined rotary and translational motion of the robot 2 along movement directions that are not parallel to the direction of the guide 7.

In particular, the carriage 62 is adapted to absorb all the forces and moments that act on the robot 2, with the exception of the force acting in the direction of the guide 7 and the twisting moment acting with respect to the rotation axis 83. In fact such force and such moment are absorbed by the gearwheel 61 and therefore passed on to the flexible threaded shafts 60, 60'.

Because they are flexible, the flexible threaded shafts 60, 60' are adapted to transfer the translation and rotation movements to the robot 2 whatever the shape assumed by the guiding and support device 1 in the active configuration.

The motor means 51 for actuating the tensioning cables 50, and the motor means 67 for actuating the flexible threaded shafts 60, 60', are advantageously arranged in the box-like body 86, which can be outside the surgical area 90.

In an embodiment of the guiding and support device 1, not shown in the accompanying figures, the motor means 51 and the motor means 67 can also be provided inside the surgical area 90.

The box-like body 86 is advantageously adapted to support the rigid bodies 3, 4, both in the inactive configuration and in the active configuration of the device 1.

The guiding and support device 1 advantageously also comprises a positioning system 8, for arranging the guiding and support device 1 with respect to the reference system of a patient.

Preferably, the positioning system 8 is rigidly coupled to the box-like body 86.

The positioning system 8 advantageously comprises a system of movement and locking 91, optionally motorized, for an arm 93 which supports the guiding and support device 1, moving it and locking it in place as needed.

The movement and locking system 91 is rigidly associated with the surgical table 92 arranged in the reference system of the patient; in fact, for the purposes of the surgical operation carried out by the robot 2 it is very important to prevent any relative movements between the patient and the movement and locking system 91.

The guiding and support device 1 advantageously also comprises one or more braking elements, which are adapted to act as a clutch between the carriage 62 (and/or the gearwheel 61) and the track 70, so as to increase the static stability of the robot 2 with respect to the guiding and support device 1.

Advantageously, furthermore, there can be a plurality of tensioning cables so that different cables can be coupled to different rigid segments of the guiding and support device. In this manner, by differently tensioning the various groups of cables it is possible to obtain a controllable tensioning on different groups of cables.

Advantageously, furthermore, according to requirements, it is possible to select, as the distal rigid segment of the guiding and support device 1, a straight rigid segment 3 or a curved rigid segment 4.

The present disclosure also relates to a robot structure that comprises a robot 2 for minimally-invasive surgery through a single parietal incision and/or natural orifice and a guiding and support device 1 as described above.

The method of introduction and use of the guiding and support device, particularly for a robot for minimally-invasive surgery through a single parietal incision and/or natural orifice such as that described in international patent application no. WO2014173932A1, is described hereinafter, with particular reference to the succession of steps illustrated in FIGS. 12 to 18.

Figure 12:
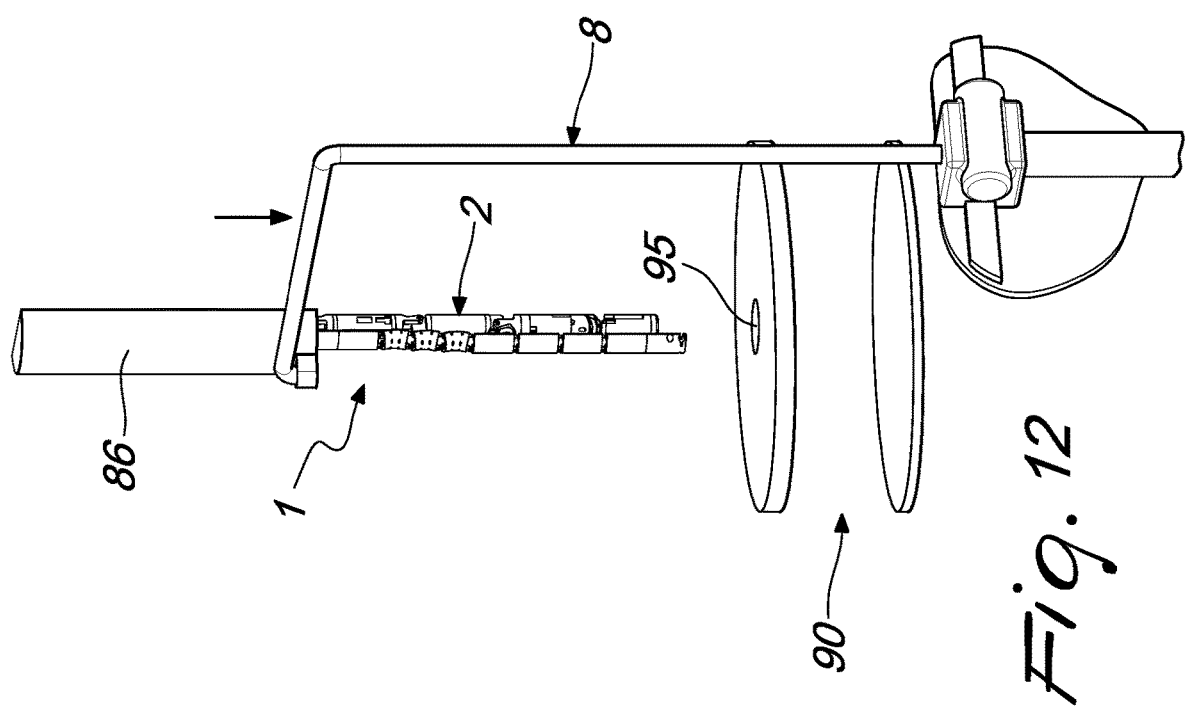

FIG. 12 illustrates the robot structure which comprises the guiding and support device 1, in the inactive configuration, with which the robot 2 is associated, both aligned with respect to the access way 95 to the surgical area 90. The robot 2 comprises a plurality of rigid segments, actively articulated to each other, by way of adapted actuators inside the segments.

Figure 13:
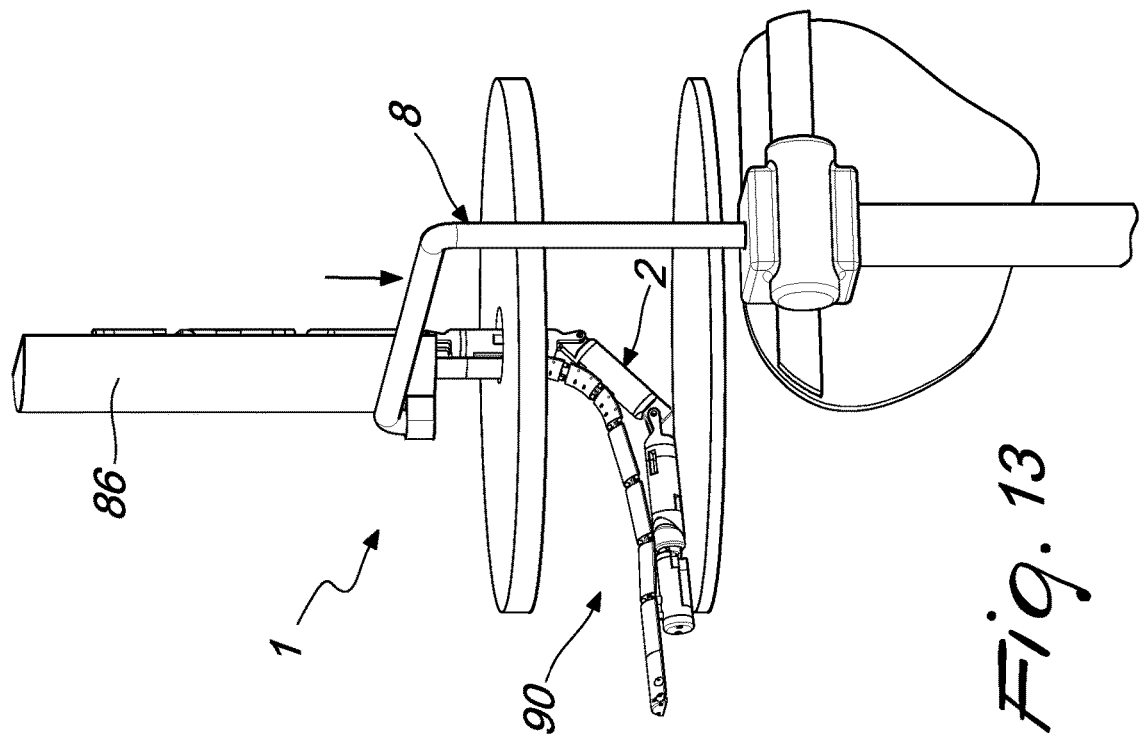

As illustrated in FIG. 12 and in FIG. 13, the positioning system 8 introduces the device 1, together with the robot 2, into the surgical area 90, through the access way 95.

As the device 1 and the robot 2 pass through the access way 95, the articulated rigid segments of the robot 2 are activated and modify the configuration of the robot 2. In this manner it is the robot 2 that modifies the configuration of the device 1 as well, so as to prevent the device 1 and/or the robot 2 from encountering unwanted obstacles during the introduction into the surgical area 90.

As illustrated in FIG. 14, when the device 1 has assumed the desired shape inside the surgical area 90, the motor means 51 are activated so that, by placing the tensioning cables 50 under tension, the device 1 assumes the rigid active configuration. At this point the guiding and support device 1 is configured to act as a guide for the complete introduction and the positioning of the robot 2, according to the curvilinear trajectory defined by the mutual approach of the rigid bodies 3, 4 which make up the guiding and support device 1.

The robot 2 can therefore be conveniently translated along the guide 7 and rotated, by way of the means for combined rotary and translational motion 6, as illustrated in FIG. 15, so as to completely enter inside the surgical area 90, as illustrated in FIG. 16, and deploy itself in an active position.

FIG. 17 also shows the step in which the robot 2 positions the container elements that contain the operating instruments, on the end rigid body 3 of the guiding and support device 1, so as to be able to retrieve the instruments necessary to carry out the surgical operation, as illustrated in FIG. 18.

It can also be seen from FIG. 15 that the robot 2, once the guiding and support device 1 is in the rigid active configuration, can emerge, with an end thereof, from the access way 95, so as to allow the substitution of the operating instruments from outside of the surgical area 90, without necessarily having to completely extract the robot 2 and the device 1 and proceed with a new introduction thereof into the surgical area 90.

FIGS. 19 and 20 show a different method of introduction of the guiding and support device 1 and of the robot 2, in which the guiding and support device 1 is first inserted through the access way 95 into the surgical area 90 and, once the device 1 assumes the adapted rigid active configuration, the robot 2 is translated along the guide 7, reaches the surgical area 90, and is deployed in the position suitable for carrying out the surgical operation.

In practice it has been found that the guiding and support device, according to the present disclosure, achieves the intended aims and advantages in that it makes it possible to introduce a robot for minimally-invasive surgery inside a surgical area in a patient, through a single parietal incision and/or by way of a natural orifice.

Another advantage of the guiding and support device, according to the disclosure, is that the device defines a curvilinear guide for the introduction of a robot for minimally-invasive surgery into a surgical area of interest according to an optimal path in order to reduce the invasiveness of the surgical operation.

Another advantage of the device, according to the disclosure, is that the device can provide a curvilinear guide of a desired length, as a function of the location of the surgical area of interest and of the path to be followed in order to reach it.

Another advantage of the device, according to the disclosure, is that it is possible to translate and/or rotate a robot for minimally-invasive surgery, along the guide defined by the device proper, by way of motor means arranged outside the surgical area of interest, thus providing a system of remote mechanical transmission of motion.

Another advantage is that the guiding and support device, according to the disclosure, is a miniaturized device.

Another advantage of the guiding and support device, according to the disclosure, is that it can be provided so that it will assume, in the active configuration, any curvilinear configuration, by conveniently selecting the rigid bodies, straight or curved, that go to make it up.

Another advantage of the guiding and support device, according to the disclosure, is that it provides a guide that enables the movement of a robot for minimally-invasive surgery in a manner that is completely stable, precise, and free from mechanical play.

The guiding and support device thus conceived is susceptible of numerous modifications and variations.

Moreover, all the details may be substituted by other, technically equivalent elements.

In practice the materials employed, provided they are compatible with the specific use, and the contingent dimensions and shapes, may be any according to requirements.

The invention claimed is:

1. A guiding and support device for a robot for minimally-invasive surgery through a single parietal incision and/or natural orifice, the guiding and support device comprising:
   a plurality of mutually associated rigid bodies,
   stiffening means associated with said guiding and support device and adapted for the transition of said device from an inactive configuration, wherein said rigid bodies move with respect to each other, to an active configuration, wherein said rigid bodies are mutually aligned so as to define a rigid guide, and vice versa, and
   means for combined rotary and translational motion which are adapted, in said active configuration of said guiding and support device, to translate and/or rotate the robot along said guide,
   wherein said means for combined rotary and translational motion comprise a pair of flexible threaded shafts, and a gearwheel configured to engage said pair of flexible threaded shafts, wherein the rotation of said flexible threaded shafts determines the translation of said gearwheel along said guide and/or the rotation of said gearwheel with respect to its own axis, said gearwheel being adapted to be associated rigidly with the robot;
   wherein said means for combined rotary and translational motion comprise a carriage configured to slide along said guide, said carriage being coupled to translate to said gearwheel and being adapted to be coupled to translate to said robot, wherein said gear wheel comprises a shaft which passes through a hole provided in said carriage, said robot being adapted to be coupled to rotate to said shaft.

2. The guiding and support device according to claim 1, wherein in each one of said rigid bodies there is at least one track, which defines said guide, and wherein said carriage comprises a plurality of wheels configured to move along said track.

3. The guiding and support device according to claim 1, wherein each one of said rigid bodies comprises a pair of longitudinal cavities which accommodate said flexible threaded shafts.

4. The guiding and support device according to claim 1, wherein said stiffening means comprise at least one tensioning cable which passes through each one of said rigid bodies and can be actuated by motor means, said active configuration being obtained by shape mating a female element with a male element of two consecutive rigid bodies.

5. The guiding and support device according to claim 1, further comprising a pair of motor means adapted to turn said flexible threaded shafts about their longitudinal axes.

6. The guiding and support device according to claim 1, wherein said rigid bodies comprise a first group of straight rigid bodies and a second group of curved rigid bodies.

7. The guiding and support device according to claim 6, wherein said straight rigid bodies and said curved rigid bodies can be mutually associated so that said rigid guide assumes a variable curvilinear configuration and has a variable length.

8. The guiding and support device according to claim 1, wherein said carriage comprises four groups of pairs of wheels, wherein each pair of wheels comprises a first wheel which has a first point of contact with a first portion of said track and a second wheel which has a second point of contact with a second portion of said track.

9. The guiding and support device according to claim 1, further comprising a positioning system for the positioning of said guiding and support device with respect to the reference system of a patient.

10. The guiding and support device according to claim 1, wherein said shaft of said gearwheel is free to slide axially with respect to said robot.

11. A robot structure, comprising a robot for minimally-invasive surgery through a single parietal incision and/or natural orifice and a guiding and support device according to claim 1.

* * * * *